United States Patent [19]
Cleveland, Jr.

[11] Patent Number: 5,254,085
[45] Date of Patent: Oct. 19, 1993

[54] ASPIRATION SYSTEM WITH POSITIVE PRESSURE

[75] Inventor: John T. Cleveland, Jr., Jacksonville, Fla.

[73] Assignee: Xomed-Treace Inc., Jacksonville, Fla.

[21] Appl. No.: 762,696

[22] Filed: Sep. 19, 1991

[51] Int. Cl.⁵ ............................................. A61M 1/00
[52] U.S. Cl. ..................................... 604/35; 604/119
[58] Field of Search ................ 604/26, 28, 33, 35, 604/118-121, 268, 317, 319, 902

[56] References Cited

U.S. PATENT DOCUMENTS

| | | | |
|---|---|---|---|
| 1,672,114 | 6/1928 | Crow | 604/249 |
| 4,315,506 | 2/1982 | Kayser et al. | 604/28 |
| 4,319,570 | 3/1982 | Grane | 604/35 |
| 4,447,226 | 5/1984 | Mayoral | 604/119 |
| 4,526,573 | 7/1985 | Lester et al. | 604/119 |
| 4,676,779 | 6/1987 | Mayoral | 604/65 |
| 4,696,669 | 9/1987 | Menhusen | 604/35 |
| 4,767,403 | 8/1988 | Hodge | 604/35 |
| 4,776,840 | 10/1988 | Freitas et al. | 604/119 |
| 4,838,281 | 6/1989 | Rogers et al. | 604/119 |
| 5,120,305 | 6/1992 | Boehringer et al. | 604/35 |

FOREIGN PATENT DOCUMENTS 1101702 3/1961 Fed. Rep. of Germany.

Primary Examiner—Ralph Lewis
Attorney, Agent, or Firm—Philip L. Rodman; Stuart E. Krieger

[57] ABSTRACT

The aspiration system with positive pressure includes a fluid flow network having a vacuum source at one end and a suction instrument at another end. Suction is regulated by a control valve that can be actuated by a foot pedal. Suction communication between the vacuum source and the suction instrument can be prevented by placing the control valve in the closed position. A positive pressure input device is included in the fluid flow network and is also actuatable by the foot pedal to provide an impulse of positive pressure at the suction instrument. The positive pressure impulse is provided when the aspiration process is being hindered by blockage of the suction inlet end of the suction instrument. A puff of positive pressure is used to expel material from the suction inlet end of the suction instrument. The use of a positive pressure impulse at the suction end of a suction instrument is also applicable to release material transported by the suction instrument from one location to another.

13 Claims, 5 Drawing Sheets

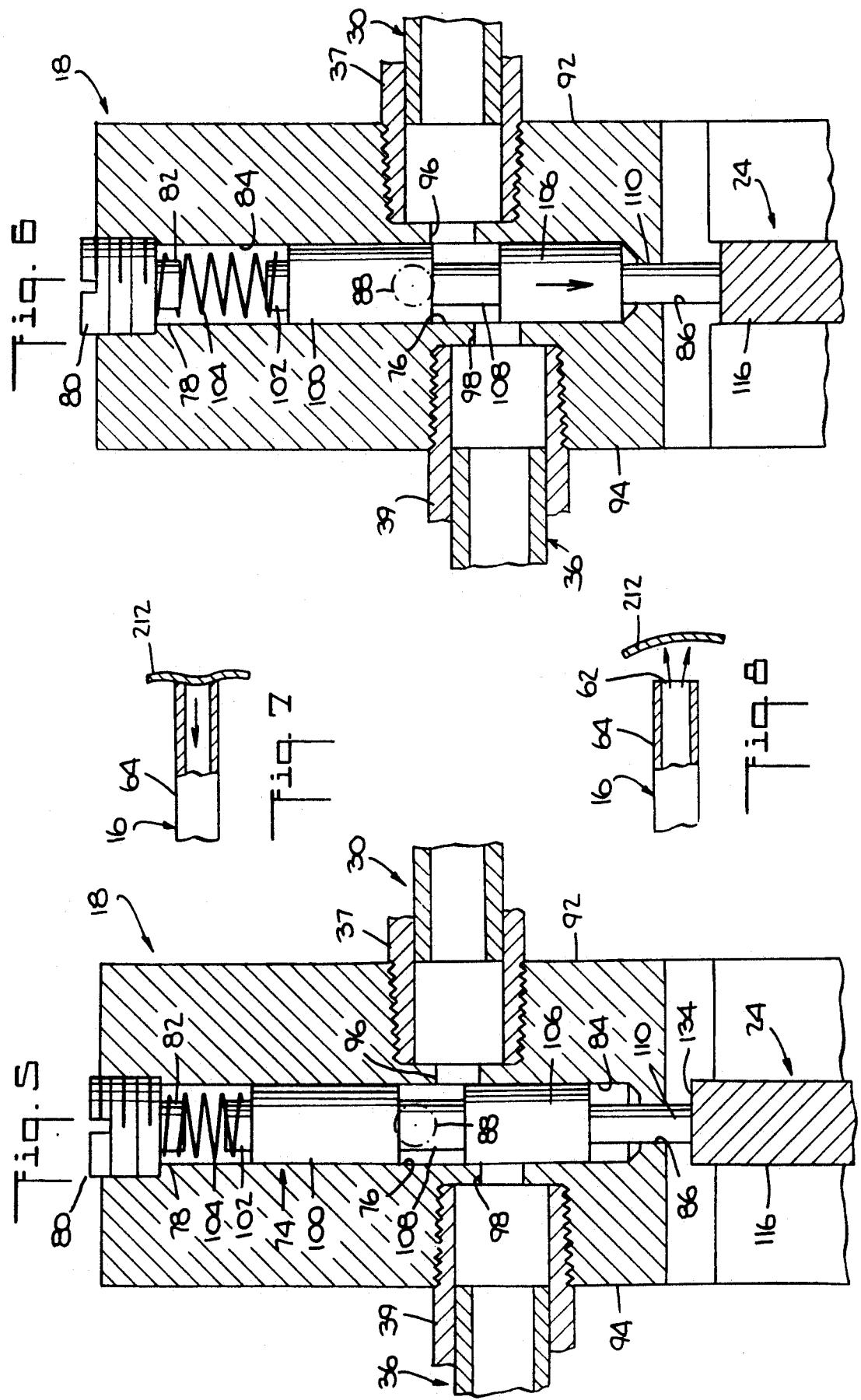

ASPIRATION SYSTEM WITH POSITIVE PRESSURE

BACKGROUND OF THE INVENTION

This invention relates to aspiration systems for removal of tissue debris and fluids from a surgical site and more particularly to an aspiration system that produces a short burst of positive pressure to release debris that blocks the suction tip of a suction instrument.

The use of aspiration in surgery to remove tissue debris and fluids from an operative site is well known. Generally, the removable debris is drawn into a suction inlet opening at the suction tip of a suction instrument for flowage to a collection container or disposal station. Oftentimes a debris particle or an agglomerate of debris becomes trapped at the suction tip and forms a blockage that hinders the aspiration process. In order to remedy this problem, the suction instrument is usually withdrawn from the surgical site to permit clean-off of the debris from the suction tip. Once the tip has been cleaned, the suction instrument can again be relocated at the surgical site for further aspiration of tissue debris and fluids.

In some instances blockage of a suction tip may occur so frequently as to necessitate periodic withdrawal of the suction instrument from the surgical site to clean off debris from the suction tip. The interruption of aspiration for purposes of cleaning a suction tip is often an inconvenience and distraction to a surgeon.

Another use of suction instruments is for the purpose of manipulating and moving small objects such as tissue grafts and parts of prosthetic devices. The small object is held by suction during movement from one location to another and a bypass or release of suction normally permits the object to drop free. In some instances, however, an object will not drop free when suction is released but will remain affixed to the suction tip because of negative pressure that remains in the suction tube. Suction grasping can thus be an unreliable procedure for moving small objects during surgery. Alternatively, the use of tweezers or other mechanical gripping devices usually does not afford the ease of manipulation of a suction tool.

One known aspiration device which includes a suction release is made by Storr's Instrument Company of St. Louis, Missouri, Part No. 1691-80, and known as the Hough-Cadogan Suction Control. The Hough-Cadogan suction control includes a foot operated suction bypass. However this unit does not have the capability of removing material that becomes affixed or attracted to a suction tip.

It is thus desirable to provide an aspiration system that produces a short burst of positive pressure directed through a suction instrument to expel, eject or release material that is trapped or otherwise affixed to the suction tip as a result of suction attraction.

OBJECTS AND SUMMARY OF THE INVENTION

Among the several objects of the invention may be noted the provision of a novel aspiration device for applying suction at the tip of a suction instrument and interrupting such suction with a short burst of positive pressure to clean or release material from the suction tip, a novel foot-controlled aspiration system that provides suction as well as a burst of positive pressure at the tip of a suction instrument, a novel aspiration system with a control valve to apply and remove negative pressure to a suction instrument and a positive pressure input device for optional use of positive pressure in the suction instrument, a novel aspiration system having a positive pressure input that can be selectively applied to a suction instrument at the option of the user, a novel method of aspirating tissue debris and fluid, and a novel method of transporting small objects from one location to another.

Other objects and features of the invention will be in part apparent and in part pointed out hereinafter.

The aspiration system in accordance with one embodiment of the invention comprises fluid flow means including a network of fluid flow tubes joined at one end to a vacuum source and joined at another end to a suction instrument. A control valve, a positive pressure input device, and a collection container are interposed in the fluid flow network between the vacuum source and the suction instrument. The control valve and the positive pressure input device are actuatable by a single actuator member preferably in the form of a foot pedal.

When the actuating pedal is in an up position or first limit position the control valve is in a closed position preventing communication between the suction source and the suction instrument. When the actuator pedal is moved from a first limit position to an intermediate limit position, the control valve is moved from its closed position to an open position thereby allowing communication between the suction source and the suction instrument.

If tissue debris or some other obstacle hampers the aspiration process by blocking a suction inlet end of the suction instrument, an impulse of positive pressure can be transmitted through the fluid flow network to the suction instrument for expulsion of positive pressure at the suction inlet end of the suction instrument. Positive pressure is thus used to clear or remove material from the inlet end of the suction instrument.

The positive pressure impulse is obtained by depressing the actuator pedal from the intermediate limit position to a second limit position to cause expansion of a diaphragm chamber which is provided along the suction flow path. With the actuator pedal located in the second limit position, a positive pressure pulsing device that includes a diaphragm member which defines a movable border of the diaphragm chamber, is positioned at the beginning of an impulse displacement cycle. Pressure on the food pedal is removed when the pulsing device is at the beginning of the impulse cycle to allow the foot pedal to return to its first limit position and thereby displace the diaphragm member to an end of impulse cycle. Return movement of the actuator pedal also operates to close the control valve while moving the pulsing member which carries the diaphragm. The closure of the control valve prevents communication between the suction source and the suction instrument and the movement of the pulsing member causes the diaphragm to compress the fluid flow chamber. An impulse of positive pressure is thus directed outwardly of the fluid flow network through the inlet end of the suction instrument.

A positive pressure impulse from the suction instrument expels debris or other material trapped or held at the suction inlet end of the suction instrument.

If a positive pressure impulse is not desired, the actuator pedal need not be depressed to the second limit position. The actuator pedal is returnable to the first limit position from the intermediate limit position to terminate the aspiration process by moving the control valve to the closed position.

Suction from the suction instrument can also be used to transport an object from one location to another. The impulse of positive pressure from the suction instrument helps release the transported object from the suction inlet end of the suction instrument to overcome any negative pressure that remains in the system after suction is bypassed or shut off.

The invention accordingly comprises the constructions and methods hereinafter described, the scope of the invention being indicated in the claims.

DESCRIPTION OF THE DRAWINGS

In the accompanying drawings,

FIG. 5 is an enlarged fragmentary detail, in section, of the control valve in a closed condition;

FIG. 6 is a view similar to FIG. 4 showing the control valve in an open condition;

FIG. 7 is a fragmentary detail, in section, of the tip end of a suction instrument with material affixed as a result of suction attraction; and, FIG. 8 is a view similar to FIG. 7 showing a positive pressure impulse being used to expel material from the suction tip.

Corresponding reference characters indicate corresponding parts throughout the several views of the drawings.

DETAILED DESCRIPTION OF THE INVENTION

Figure 1:
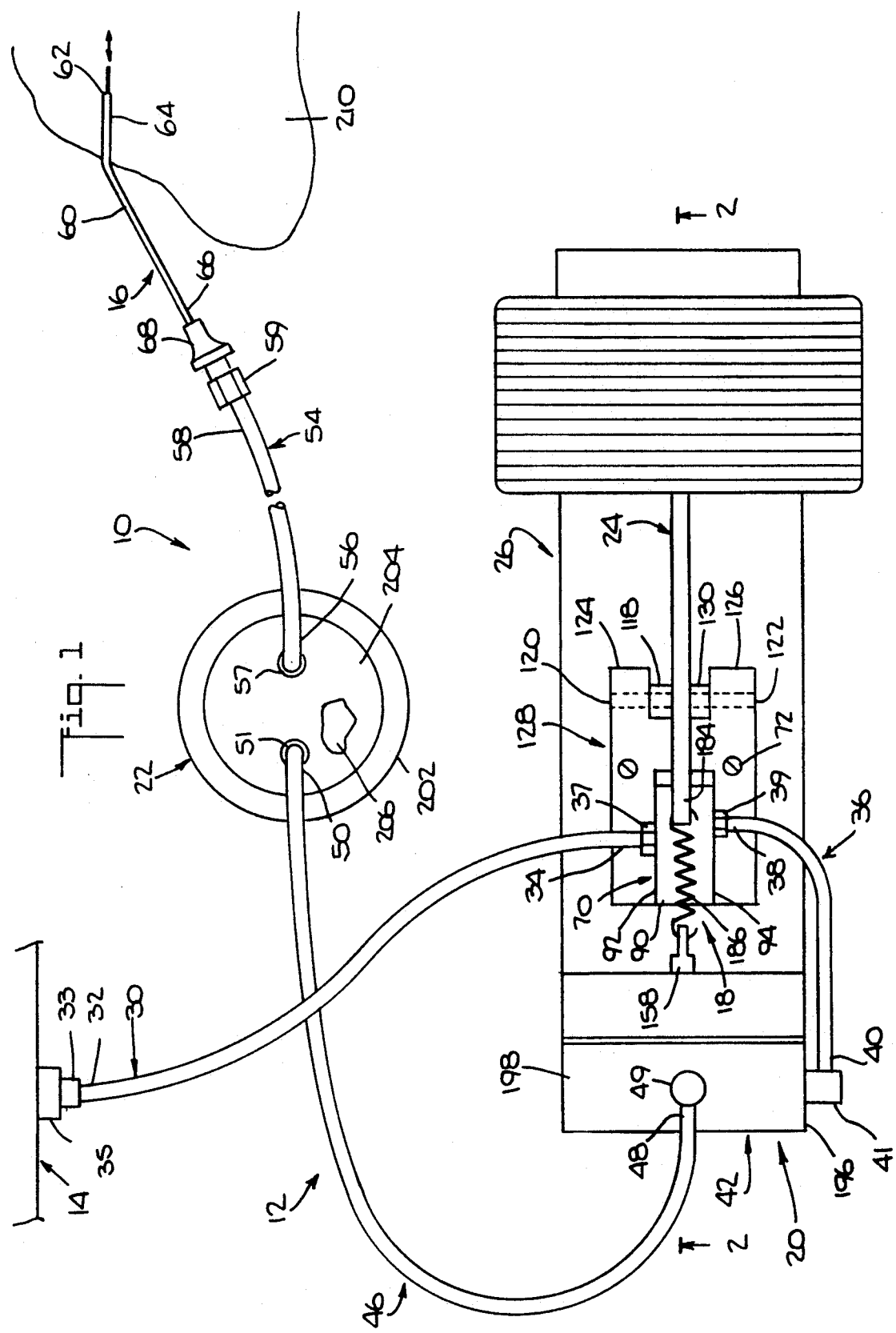
FIG. 1 is a simplified schematic view of a system for aspirating tissue debris and fluid from a surgical site which incorporates one embodiment of the present invention.

An aspiration system for aspirating tissue debris and fluid from a surgical site incorporating one embodiment of the invention is generally indicated by the reference number 10 in FIG. 1.

The system 10 comprises fluid flow means 12 including a network of tubes 30, 36, 46 and 54. The fluid flow means 12 is joined at one end to a vacuum or suction source 14 and joined at another end to a suction instrument 16.

A control valve 18, a positive pressure input device 20, and a collection container 22 are interposed in the fluid flow means 12 between the vacuum source 14 and the suction instrument 16.

An actuator 24 for actuating movement of the control valve 18 from an open position to a closed position and for causing movement of the positive pressure input device 20 is pivoted to a base plate 26.

The fluid flow means 12 includes a tube 30 having one end 32 connected to a fitting 33 that detachably engages a connector 35 at the vacuum source 14. An opposite end 34 of the tube 30 is connected to a fitting 37 at one side of the control valve 18. A tube 36 communicable with the tube 30 includes one end 38 connected to a fitting 39 at a second side of the control valve 18 and an opposite end 40 connected to a fitting 41 in a cylindrical housing 42 of the positive pressure input device 20.

A further tube 46 communicable with the tube 36 includes one end 48 connected to a fitting 49 on the housing 42 and an opposite end 50 connected to a fitting 51 in the collection container 22. Still another tube 54 communicable with the tube 46 is connected at one end 56 to a fitting 57 in the collection container 22 and an opposite end 58 connected to a fitting 59 joined to the suction instrument 16.

The vacuum suction source 14 is a conventional vacuum source, usually provided in an operating room from a wall outlet and providing suction in the range of 300 to 600 mm. Hg negative pressure at the suction source.

The suction instrument 16 includes a needle or tube 60, preferably formed of stainless steel and having an approximate 0.9 mm. external diameter and an approximate 0.8 mm. internal diameter. An inlet suction opening 62 is provided at an end portion 64 of the needle 60. An opposite end 66 of the needle 60 is joined to a conventional adapter member 68 that engages the fitting 59.

Figure 2:
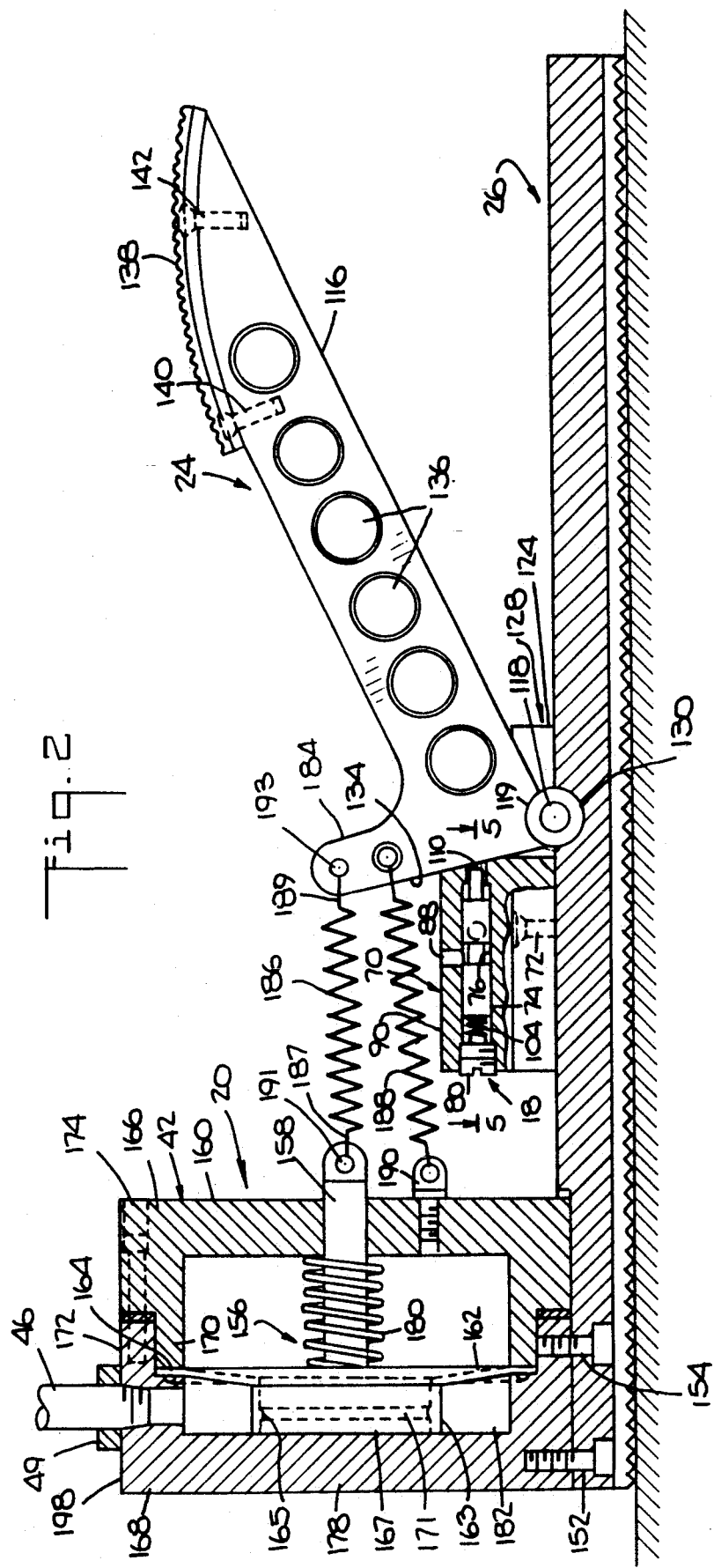
FIG. 2 is a sectional view taken on the line 2-2 of FIG. 1 showing a control valve in a closed condition, and a positive pressure impulse device.

Referring to FIGS. 2-6, the control valve 18 includes a housing 70 joined to the base plate 26 by a fastener such as the fastener 72 (FIG. 2). A valve member 74 of the valve 18 is slidably disposed in an elongated bore 76 of the housing 70. An end 78 (FIGS. 5 and 6) of the bore 76 is closed by a threaded cap 80 having an inwardly projecting stub 82 of reduced diameter. An opposite end 84 of the bore 76 has a reduced diameter extension portion 86 that opens outwardly of the housing 70.

The housing 70 also includes a vent opening 88 at an upper surface 90. The tube sections 30 and 36 are offset a predetermined amount from each other at respective sides 92 and 94 of the housing 70. The tube section 30 communicates with a valve port 96 and the tube section 36 communicates with a valve port 98. The vent opening 88 is offset a predetermined amount from the valve port 96.

The valve member 74 includes an air vent closure head 100 having a reduced diameter stub portion 102 extending toward the stub portion 82 of the threaded cap 80. A biasing spring 104 is mounted on the respective stub portions 82 and 102 to bias the valve member 74 into an open position. The valve member 74 further includes a valve port closure head 106 spaced from the air vent closure head 100 by a reduced neck portion 108 of predetermined axial extent. An engagement stem 110 of the valve member 74 extends from the valve port closure head 106 outwardly of the housing 70 from the extension portion 86 for engagement with the actuator 24 under the influence of the biasing spring 104.

The actuator 24, which is in the form of a foot pedal, includes a flange portion 116 pivoted at the base plate 26 by means of a pivot member 118. The pivot member 118 has end portions 120 and 122 (FIG. 1) fixed to respective ear portions 124 and 126 of a pivot block 128 fastened to the base plate 26 in any suitable known manner. The pivot member 118 is confined in a bushing 119 fixed to the flange 116 and extending between the ear portions 124 and 126. A suitable curved recess 130 (FIG. 2) is formed in the base plate 26 to accommodate the bushing 119.

Preferably, the pivot block 128 and the valve housing 70 are formed as an integral unit.

The flange portion 116 of the actuator member 24 includes an end surface 134 that engages the engagement stem 110 of the valve member 74. The flange portion 116 includes weight reduction holes 136 and a tread piece 138 fastened to the flange 116 by fasteners such as 140 and 142 (FIG. 2).

The housing 42 of the positive pressure input device 20 is fastened to the base plate 26 by fasteners such as 152 and 154. A pulsing device 156 provided in the housing 42 includes a rod 158 slidably mounted in a wall 160. A flexible diaphragm member 162 formed of silicone for example, is joined to the rod 158 in any suitable known manner. The diaphragm 162 includes a molded annular flange 163 having a circular radially inwardly projecting formation 165 that engages a complementary shaped circular groove 171 of a cylindrical piston member 167. The piston member 167, which can be formed of stainless steel, is thus detented in the annular flange 163 of the diaphragm 162 stopping displacement of the diaphragm member 162.

A peripheral portion 164 of the diaphragm 162 which is of circular shape is sandwiched between cylindrical shell halves 166 and 168 of the housing 42. The shell half 166 includes a step-like section 170 that mates with a corresponding step-like section 172 on the shell half 168. The shell halves 166 and 168 are joined together by a fastener such as 174 such that the diaphragm periphery 164 is tightly sandwiched between the shell halves.

The piston member 167 normally engages a wall 178 of the housing 42 under the influence of a biasing spring 180 disposed between the diaphragm 162 and the wall 160 and supported on the rod 158. The piston member 167 functions as a stop member for stopping displacement of the diaphragm member 162 toward the wall 178. A fluid flow chamber 182 is defined between the diaphragm 162 and the wall 178.

An end portion of the rod 158 projects beyond the wall 160 of the housing 42 and is connected to an appendage 184 of the flange 116 by a spring 186. A predetermined clearance is provided between the attachment ends 187 and 189 of the spring 186 and the eyelets 191 and 193 in the respective rod 158 and appendage 184.

A return spring 188 connects the appendage 184 with the wall 160 at an eyepiece 190.

The tube 36 is joined to a side wall 196 (FIG. 1) of the housing 42 in alignment with the fluid flow chamber 182. The fluid flow section 46 is joined to a top wall 198 of the housing 42, also in alignment with the fluid flow chamber 182. Under this arrangement the tubes 36 and 46 communicate with each other through the fluid flow chamber 182.

The collection container 22 includes a generally cylindrical body portion 202 and a lid member 204 that is sealed to the body portion in substantially leak-tight arrangement. The tubes 46 and 54 communicate with each other through the chamber 206 of the collection container. 22.

When the system 10 is not in use, the valve 18 is in a normally closed position as shown in FIG. 5 and the actuator pedal 24 is in the up position or non-depressed limit position of FIG. 2. Suction communication between the vacuum source 14 and the suction instrument 16 does not occur because the valve member 74 is in the closed position of FIG. 4. The valve member 74 thus blocks the valve port 98 and prevents communication between the tubes 30 and 36.

The valve member 74 is maintained in its the closed position of FIG. 5, which corresponds to the non-depressed limit position of the actuator pedal 24 of FIG. 2, by engagement of the end surface 134 of the actuator pedal 24 with the engagement stem 110 of the valve member 74. The valve biasing spring 104 is of a selected strength which cannot overcome the holding force of the actuator pedal return spring 188. The valve port closure head 106 of the valve member 74 thus blocks the valve port 98 when the valve member 74 is in its closed position. Also, with the valve member 74 in the closed position the vent opening 88 aligns with the reduced diameter stem portion 108 to permit venting of the tube 30.

Figure 3:
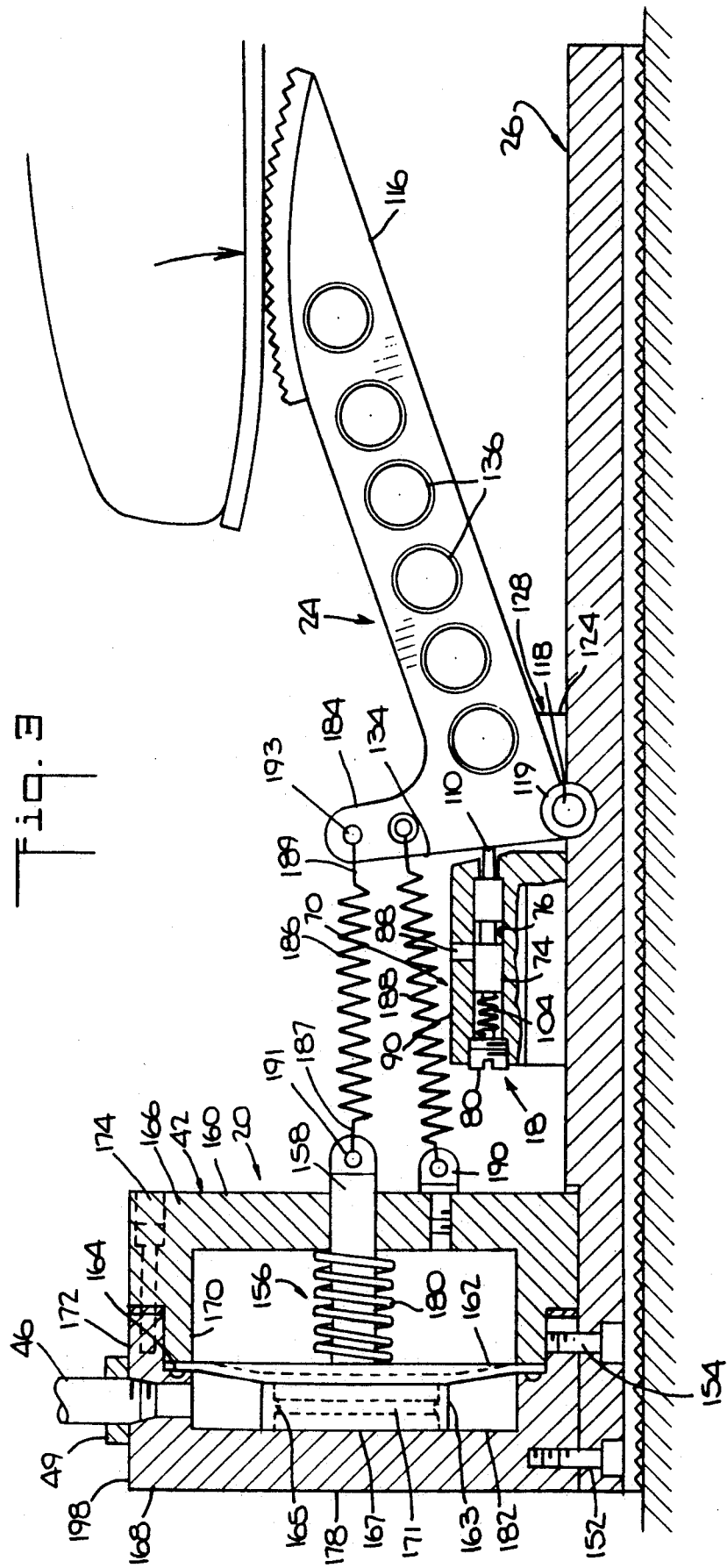
FIG. 3 is a view similar to FIG. 2 showing the control valve actuated to an open condition by a foot pedal actuator.

In using the system 10, when suction is desired at the suction instrument 16, the actuator pedal 24 is depressed from the first limit position of FIG. 2 to a predetermined intermediate limit position of FIG. 3. Movement of the pedal 24 from the first limit position to the intermediate limit position allows the valve biasing spring 104 to displace the valve member 74 from the closed position of FIG. 5 to the open position of FIG. 6.

Displacement of the valve member 74 is controlled by the position of the actuator pedal 24. Thus, as the actuator pedal 24 is pivoted in a clockwise direction with reference to FIG. 2, the reduced stem portion 108 of the valve member 74 aligns with the valve ports 96 and 98. The tubes 30 and 36 can then communicate with each other through the valve ports 96 and 98 and across the reduced stem 108.

It should be noted that the valve 18 is preferably of a size that requires only approximately 1.6 mm. displacement of the valve member 74 to transition the valve 18 from the closed position of FIGS. 2 and 5 to the open position of FIGS. 3 and 6. Since the total displacement of the valve member is relatively small, for purposes of simplicity the valve positions are referred to as discrete open and closed positions. The open position of the valve member 74 as shown in FIG. 6 is where the valve port closure head 106 bottoms against the end of the bore 84. The position of the actuator pedal 24 as shown in FIG. 3 which corresponds to the open position of the valve member 74 as shown in FIG. 6, is referred to as the intermediate limit position. It will also be noted that the first limit position of the actuator pedal 24, wherein the valve member 74 is closed as in FIG. 2, also corresponds to a position of the diaphragm 162 wherein the piston member 167, which functions as a stop member, engages the wall 168 of the housing 42.

As the actuator pedal 24 moves from the first limit position of FIG. 2 to the intermediate limit position of FIG. 3, wherein displacement of the pedal 24 is preferably approximately 1 cm., the return spring 188 stretches whereas the spring 186 remains relaxed. The spring 186 does not stretch during movement of the pedal 24 from the first limit position to the intermediate limit position due to a predetermined clearance in the connections of the spring ends 187 and 189 to the rod 158 and the actuator pedal appendage 184. Thus, during movement of the actuator pedal 24 from the first limit position to the intermediate limit position, there is no movement of the pulsing device 156. Consequently the diaphragm piston member 167 remains in contact with the wall 168.

Figure 4:
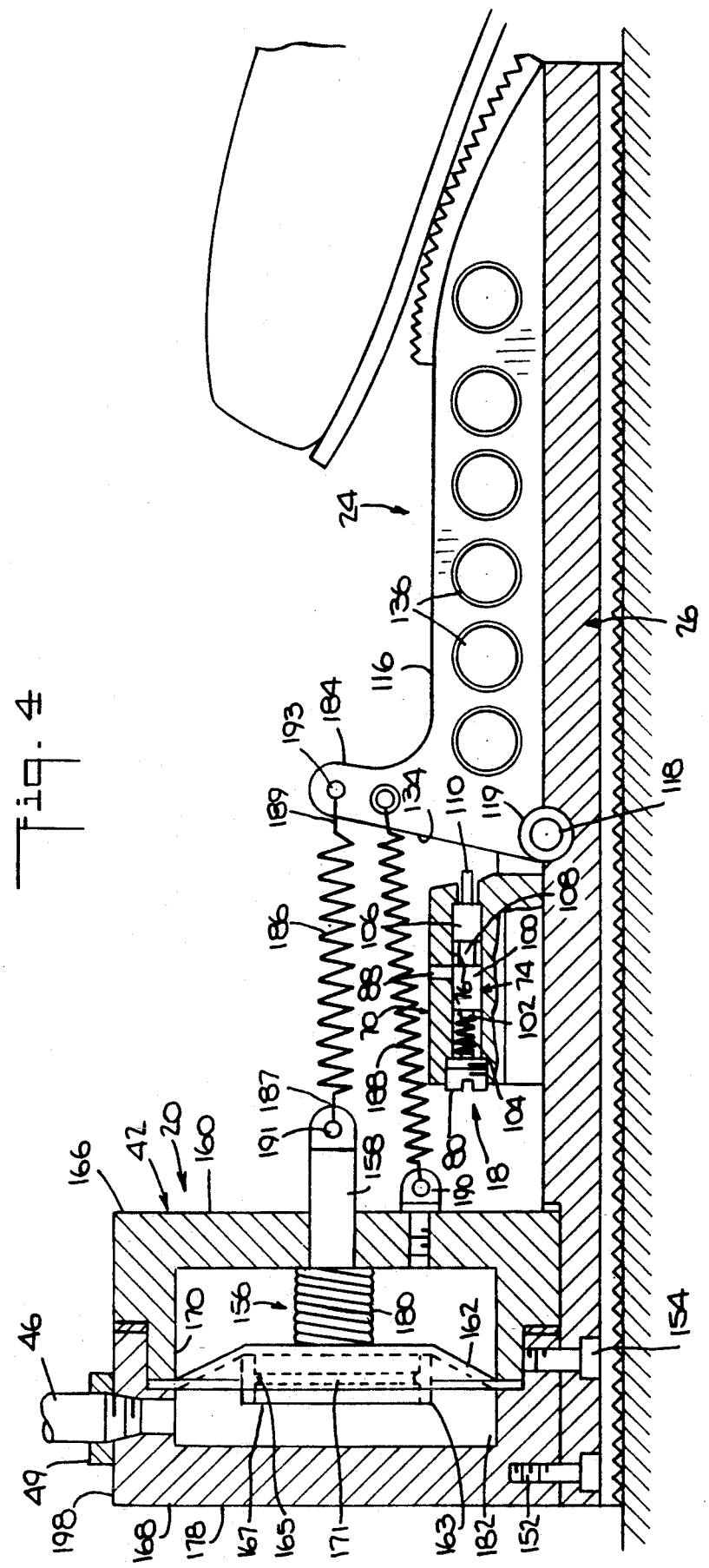
FIG. 4 is a view similar to FIG. 3 showing the control valve in an open condition and the positive pressure impulse device positioned to begin an input pulse.

Once the actuator pedal 24 is further depressed in a clockwise direction from the intermediate limit position of FIG. 3 to the second limit position of FIG. 4, the spring 186 is stretched. The spring 186 thus pulls the rod 158 to the right as shown in FIG. 4 to overcome the force of the biasing spring 180 and displace the diaphragm 162 from the position of FIGS. 2 and 3 to the position of FIG. 4, which corresponds to the second limit position of the actuator pedal 24.

As the actuator pedal 24 moves from the intermediate limit position of FIG. 3 to the second limit position of FIG. 4, the valve member 74 remains in the open position of FIG. 6 under the influence of the valve biasing spring 82.

The spring constant of the spring 186 is sufficiently greater by a predetermined amount than that of the return spring 188 to enable the user to easily discern when the actuator pedal 24 is being moved beyond the intermediate limit position of FIG. 3 toward the second limit position of FIG. 4. Thus the force required at the actuator pedal 24 to displace the diaphragm 162 is substantially greater than that required to move the actuator pedal 24 from the first limit position of FIG. 2 to the intermediate limit position of FIG. 3.

When it is desired to apply suction at the surgical instrument 16, the actuator pedal 24 is depressed a predetermined amount such as 1 cm. to move the valve member 74 from its closed position to its open position. With the valve member 74 in the open position of FIGS. 3 and 6, suction from the vacuum source 14 is transmissible through the suction opening 62 of the suction instrument 16 to draw in tissue debris and fluid from a surgical site 210. The withdrawn material (not shown) flows through the needle 60 into the tube 54 and is deposited into the chamber 206 of the collection container 22.

Suction is further transmitted through the tube 46 to the fluid flow chamber 182 of the positive pressure input device housing 42. The suction path further continues from the fluid flow chamber 182 through the tube 36, the valve port 98, across the reduced stem portion 108 of the valve member 74 into the valve port 96, through the tube 30 and to the vacuum source 14.

This suction flow path continues to draw material into the inlet opening 62 of the suction instrument 16 as long as the valve 18 is in the open position of FIG. 6 wherein the actuator pedal 24 is depressed to the intermediate limit position of FIG. 3. Once there is no further need for suction the force on the actuator pedal 24 can be relaxed to allow the return spring 188 to return the actuator pedal 24 to the first limit position of FIG. 2.

During the aspiration process, it may become apparent that aspiration is hampered because of a blockage of the suction inlet opening 62 of the needle 60 by tissue debris. The actuator pedal 24 can be depressed beyond the intermediate limit position of FIG. 3 to the second limit position of FIG. 4 and then released to allow the pedal 24 to return to the first limit position of FIG. 2.

Depression of the pedal 24 beyond the intermediate limit position of FIG. 3 places a tension on the spring 186 causing displacement of the rod 158 of the pulsing device 156 to the right as viewed in FIG. 4. Displacement of the rod 158 causes the diaphragm 162 to move from the position of FIGS. 2 and 3 to the position of FIG. 4, thereby expanding the volume of the fluid flow chamber 182 a predetermined amount.

Subsequent release of the pedal 24 enables the springs 186 and 188 to return the pedal 24 to the first limit position of FIG. 2 thereby displacing the rod 158 to the left from the position of FIG. 4. The diaphragm 162 is thus displaced toward the wall 178 to reduce the volume of the diaphragm chamber 182 and enable any air trapped in the diaphragm chamber 182 to be forced through the tubular section 46 toward the suction instrument 16. Air trapped in the diaphragm chamber 182 is expelled from the suction inlet opening 62 of the needle 60 because the valve member 74 resumes its closed position of FIG. 5 as the diaphragm 162 displaces from the position of FIG. 4 to the position of FIG. 2. The valve port 98 is thus blocked by the valve port closure head 106 when the actuator pedal 24 is permitted to return to the first limit position and since the air trapped in the diaphragm chamber 182 is blocked by the valve 74, such air can only be expelled through the suction instrument 16.

It should be noted that the availability of air in the diaphragm chamber 182 is attributable to a less than perfect vacuum condition existing in the aspiration system. The impulse of positive pressure through the tubes 46 and 58 toward the suction instrument 16 amounts to a positive puff of pressure as the pedal 24 returns to the first limit position of FIG. 1. This puff of pressure is usually sufficient to release debris attracted to the suction inlet opening 62 of the suction needle 60 during an aspiration process in the manner shown in FIGS. 6 and 7. The puff of positive pressure is also useful to permit release of objects such as tissue member 212 held by suction as shown in FIG. 7 and being transported on the suction instrument 16 from one location to another. The tissue 212 is expelled by a puff of positive pressure from the suction inlet opening 62 as shown in FIG. 8.

Some advantages of the present invention evident from the foregoing description include a release feature for removing debris or other materials from the suction inlet opening of a suction instrument by use of a positive pressure. The possibility of contamination due to manual clean-off of a suction instrument is thus substantially reduced since there is no need to withdraw the suction instrument from a surgical site to clean off trapped debris. Another advantage is that the positive pressure feature is a selectable option to be used only when necessary. A further advantage is that the aspiration system is controlled by foot pedal actuation, is relatively easy to operate and does not require power switches or other electrical components since the system is mechanically operated.

In view of the above, it will be seen that the several objects of the invention are achieved and other advantageous results attained.

As various changes can be made in the above constructions and methods without departing from the scope of the invention, it is intended that all matter contained in the above description or shown in the accompanying drawings shall be interpreted as illustrative and not in a limiting sense.

What is claimed is:

1. An aspiration system comprising,
   a) a valve having an open position and a closed position,
   b) fluid flow means including a first fluid flow portion on a first side of said valve communicable with a suction source, and a second fluid flow portion on a second side of said valve communicable with a suction instrument,
   c) a positive pressure input means being communicable with said second fluid flow portion for inducing a pulse of positive pressure in said second fluid flow portion when said valve is in said closed position,
   d) said first and second fluid flow portions being communicable through said valve when said valve is in said open position, said first and second fluid flow portions being non-communicable when said valve is in said closed position, e) actuating means for actuating movement of said valve from one of said positions to the other of said positions and for actuating said positive pressure input means to cause said positive pressure input means to induce said pulse of positive pressure in said second fluid flow portion, said actuating means being voluntarily actuatable the discretion of an operator to open and close said valve and to cause said positive pressure input means to induce said pulse of positive pressure in said second fluid flow portion, f) and wherein said actuating means comprise an actuating member pivotable with respect to said valve from a first limit position, wherein said valve is in said closed position, to a second limit position, wherein said valve is in said open position, and to a predetermined intermediate limit position between said first and second positions, wherein said valve remains in said open position during the course of movement of said actuating member from said second limit position to said intermediate limit position and vice versa, g) and wherein said actuating member is connected to said positive pressure input means to cause movement of said positive pressure input means to generate said pulse of positive pressure in said second fluid flow portion, said positive pressure input means having an end of input pulse position, wherein no positive pressure pulse can be generated, said end of input pulse position corresponding to the first limit position of said actuating member, said positive pressure input means being movable from said end of input pulse position to a beginning of input pulse position, wherein a positive pressure pulse can be generated, said beginning of input pulse position corresponding to the second limit position of said actuating member, and h) wherein said positive pressure input means includes a movable pulsing member, means for connecting said actuating member to said movable pulsing member such that said pulsing member remains motionless in said end of input pulse position while said actuating member moves from said first limit position to said intermediate limit position, said connection means enabling said actuating member to cause movement of said pulsing member from said end of input pulse position to said beginning of input pulse position when said actuating member pivots from said intermediate limit position to said second limit position, reverse movement of said actuating member from said second limit position to said first limit position enabling said pulsing member to move from said beginning of input pulse position to said end of input pulse position to generate said pulse of positive pressure.

2. An aspiration system comprising, a) a valve having an open position and a closed position, b) fluid flow means including a first fluid flow portion on a first side of said valve communicable with a suction source, and a second fluid flow portion on a second side of said valve communicable with a suction instrument, c) a positive pressure input means being communicable with said second fluid flow portion for inducing a pulse of positive pressure in said second fluid flow portion when said valve is in said closed position, d) said first and second fluid flow portions being communicable through said valve when said valve is in said open position, said first and second fluid flow portions being non-communicable when said valve is in said closed position, e) actuating means for actuating movement of said valve from one of said positions to the other of said positions and for actuating said positive pressure input means to cause said positive pressure input means to induce said pulse of positive pressure in said second fluid flow portion, said actuating means being voluntarily actuatable at the discretion of an operator to open and close said valve and to cause said positive pressure input means to induce said pulse of positive pressure in said second fluid flow portion, f) and wherein said actuating means comprise an actuating member pivotable with respect to said valve from a first limit position, wherein said valve is in said closed position, to a second limit position, wherein said valve is in said open position, and to a predetermined intermediate limit position between said first and second positions, wherein said valve remains in said open position during the course of movement of said actuating member from said second limit position to said intermediate limit position and vice versa, and g) wherein said positive pressure input means includes a pulsing member connected to said actuating member by a resilient member, biasing means for biasing said pulsing member in an end of input pulse position when said actuating member is moved from said first limit position to said intermediate limit position, said pulsing member being moved by said actuating member and said resilient member from said end of pulse position to a beginning of input pulse position when said actuating member is moved from said intermediate limit position to said second limit position to overcome the biasing means.

3. The aspiration system as claimed in claim 1 wherein said valve is in a closed condition when said actuating member is in said first limit position, said valve being biased to move to said open condition when said actuating member moves from said first limit position to said intermediate limit position.

4. The aspiration system as claimed in claim 2 wherein said actuating member is movable with respect to said pulsing member a first predetermined amount in a predetermined direction from the first limit position to the second limit position without causing said pulsing member to induce said pulse of positive pressure in said second fluid flow portion, and said actuating member is thereafter movable a second predetermined amount in a direction opposite said predetermined direction to cause said pulsing member to induce said pulse of positive pressure in said second fluid flow portion.

5. The aspiration system as claimed in claim 2 wherein said positive pressure input means includes a movable pressure input member and said actuating means is engagable with said valve to move said valve from said closed position to said open position, and said actuating means is engageable with said pressure input member to move said pressure input member only after said actuating means moves said valve from said closed position to said open position.

6. The aspiration system as claimed in claim 2 wherein said actuating member is connected to said positive pressure input means to cause movement of said pulsing member to generate said pulse of positive pressure in said second fluid flow portion, said pulsing member having an end of input pulse position wherein no positive pressure pulse can be generated, said end of input pulse position corresponding to the first limit position of said actuating member, said pulsing member being movable from said end of input pulse position to a beginning of input pulse position wherein a positive pressure pulse can be generated, said beginning of input pulse position corresponding to the second limit position of said actuating member.

7. The aspiration system as claimed in claim 2 wherein said positive pressure input means is at the second flow portion of said fluid flow means and said positive pressure input means include a fluid flow chamber communicable with said valve when said valve is in said open position, and said pulsing member includes a diaphragm provided at one end of said fluid flow chamber, said diaphragm being movable to expand to the volume of said fluid flow chamber when said actuating member is moved from said first limit position to said second limit position.

8. The aspiration system as claimed in claim 7 wherein said positive pressure input means include biasing means for biasing said diaphragm in a volume decreasing direction that decreases the volume of said fluid flow chamber, said diaphragm being movable in said volume deceasing direction when said actuator member is moved from said second limit position to said first limit position.

9. The aspiration system as claimed in claim 2 wherein said positive pressure input means includes means for connecting said actuating means to said movable pulsing member such that said pulsing member remains motionless in said end of input pulse position while said actuating member moves from said first limit position to said intermediate limit position, said connection means enabling said actuating member to cause movement of said pulsing member from said end of input pulse position to said beginning of input pulse position when said actuating member pivots from said intermediate limit position to said second limit position, reverse movement of said actuating member from said second limit position to said first limit position enabling said pulsing member to move from said beginning of input pulse position to said end of input pulse position to generate said pulse of positive pressure.

10. An aspiration system comprising,
a) a valve having an open position and a closed position,
b) fluid.flow means including a first fluid flow portion on a first side of said valve and a second fluid flow portion on a second side of said valve, said first and second fluid flow portions being communicable when said valve is in said open position and being non-communicable when said valve is in said closed position,
c) said first fluid flow portion being communicable with a suction source,
d) a suction member connected to said second fluid flow portion and having a suction inlet end, said suction member being communicable with said first fluid flow portion when said valve is in said open position,
e) a positive pressure input means communicable with said second fluid flow portion to permit inducement of positive pressure in said suction member when said valve is in said closed position, and
f) voluntarily actuatable actuating means for actuating movement of said valve from said open position to said closed position, and for actuating said positive pressure input means to induce positive pressure in said second fluid flow portion when said valve is moved to said closed position,
g) and wherein said actuating means comprise a pivotal pedal member pivotable with respect to said valve and normally biased to a first limit position wherein said valve is in said closed position, said pedal member being movable toward a second limit position to permit movement of said valve to said open position, and
h) wherein said positive pressure input means is in the second fluid flow portion of said fluid flow means and said positive pressure input means includes a fluid flow chamber communicable with said valve when said value is in said open position, and a pulsing member is movable in said fluid flow chamber, said pulsing member being connected to said pedal member and including a flexible diaphragm at one end of said fluid flow chamber, said diaphragm being displaceable a predetermined distance to expand the volume of said fluid flow chamber when said pedal member moves from said first limit position to said second limit position, return movement of said pedal member from said second limit position to said first limit position permitting movement of said flexible diaphragm to decrease the volume of said fluid flow chamber and cause an impulse of positive pressure in said fluid flow means directed to said suction member for expulsion at said suction inlet end.

11. The aspiration system as claimed in claim 10 wherein said valve member is biased to move from said closed position to said open position when said pedal member moves from said first limit position to said second limit position.

12. The aspiration system as claimed in claim 10 wherein said pedal member has a predetermined intermediate limit position between said first and second limit positions wherein said valve member is in said open position.

13. The aspiration system as claimed in claim 10 wherein said positive pressure input means includes a movable pulsing member having an end of input pulse position corresponding to the first limit position of said pedal member, means for connecting said pedal member to said movable pulsing member such that said pulsing member remains motionless in said end of input pulse position while said pedal member moves from said first limit position to said intermediate limit position, said connection means enabling said pedal member to cause movement of said pulsing member from said end of input pulse position to a beginning of input pulse position when said pedal member pivots from said intermediate limit position to said second limit position, reverse movement of said pedal member from said second limit position to said first limit position enabling said pulsing member to move from said beginning of input pulse position to said end of input pulse position to generate said pulse of positive pressure.

* * * * *